United States Patent [19]

Jensen et al.

[11] 4,411,659
[45] Oct. 25, 1983

[54] DRAINABLE COLLECTION POUCH AND FILTER ASSEMBLY THEREFOR

[75] Inventors: Marvin E. Jensen, Niles; Mahmood Mohiuddin, Lake Zurich, both of Ill.

[73] Assignee: Hollister Incorporated, Libertyville, Ill.

[21] Appl. No.: 358,819

[22] Filed: Mar. 16, 1982

[51] Int. Cl.³ .............................................. A61F 5/44
[52] U.S. Cl. .................................. 604/332; 604/333; 604/340
[58] Field of Search ............... 604/276, 317, 332–345; 162/117; 604/359; 4/144.1; 55/387; 24/248 R

[56] References Cited

U.S. PATENT DOCUMENTS

| | | | |
|---|---|---|---|
| 2,054,535 | 9/1936 | Diack | 604/333 |
| 2,555,086 | 5/1951 | Guinn | 604/333 |
| 3,039,464 | 6/1962 | Galindo | 604/344 |
| 3,055,368 | 9/1962 | Baxter | 604/344 |
| 3,084,091 | 4/1963 | Volkman et al. | 162/117 X |
| 3,439,677 | 4/1969 | Bonfils | 604/333 |
| 3,523,534 | 8/1970 | Nolan | 24/248 R X |
| 3,613,123 | 10/1971 | Langstrom | 4/144.1 X |
| 3,759,260 | 9/1973 | Nolan et al. | 604/333 |
| 3,780,739 | 12/1973 | Frank | 604/335 |
| 3,804,091 | 4/1974 | Nolan et al. | 604/333 |
| 3,822,704 | 7/1974 | Nolan | 604/339 |
| 3,841,332 | 10/1974 | Treacle | 604/335 |
| 3,902,496 | 9/1975 | Eakin | 604/334 |
| 3,941,133 | 3/1976 | Chen | 604/336 |
| 3,952,727 | 4/1976 | Nolan | 604/333 |
| 4,084,590 | 4/1978 | Caraway et al. | 604/335 |
| 4,203,445 | 5/1980 | Jessup et al. | 604/333 |
| 4,213,458 | 7/1980 | Nolan et al. | 604/344 |
| 4,274,848 | 6/1981 | LaGro | 55/387 |
| 4,280,498 | 7/1981 | Jensen | 604/335 |
| 4,300,560 | 11/1981 | Steer et al. | 604/335 |

*Primary Examiner*—Gregory E. McNeill
*Assistant Examiner*—Michelle N. Lester
*Attorney, Agent, or Firm*—Tilton, Fallon, Lungmus

[57] ABSTRACT

A collection pouch for use by ostomates, the pouch being drainable to facilitate extended use of the pouch and including a gas venting and filtering assembly having a replaceable deodorizing filter element. A barrier film is disposed within the pouch to protect the filter element from contact with and possible obstruction by exudate. Interior wall surface areas of the double-chambered pouch are raised or embossed, and the filter assembly is internally ribbed, to insure that the pathway for the escape of gases from the pouch remains open.

29 Claims, 7 Drawing Figures

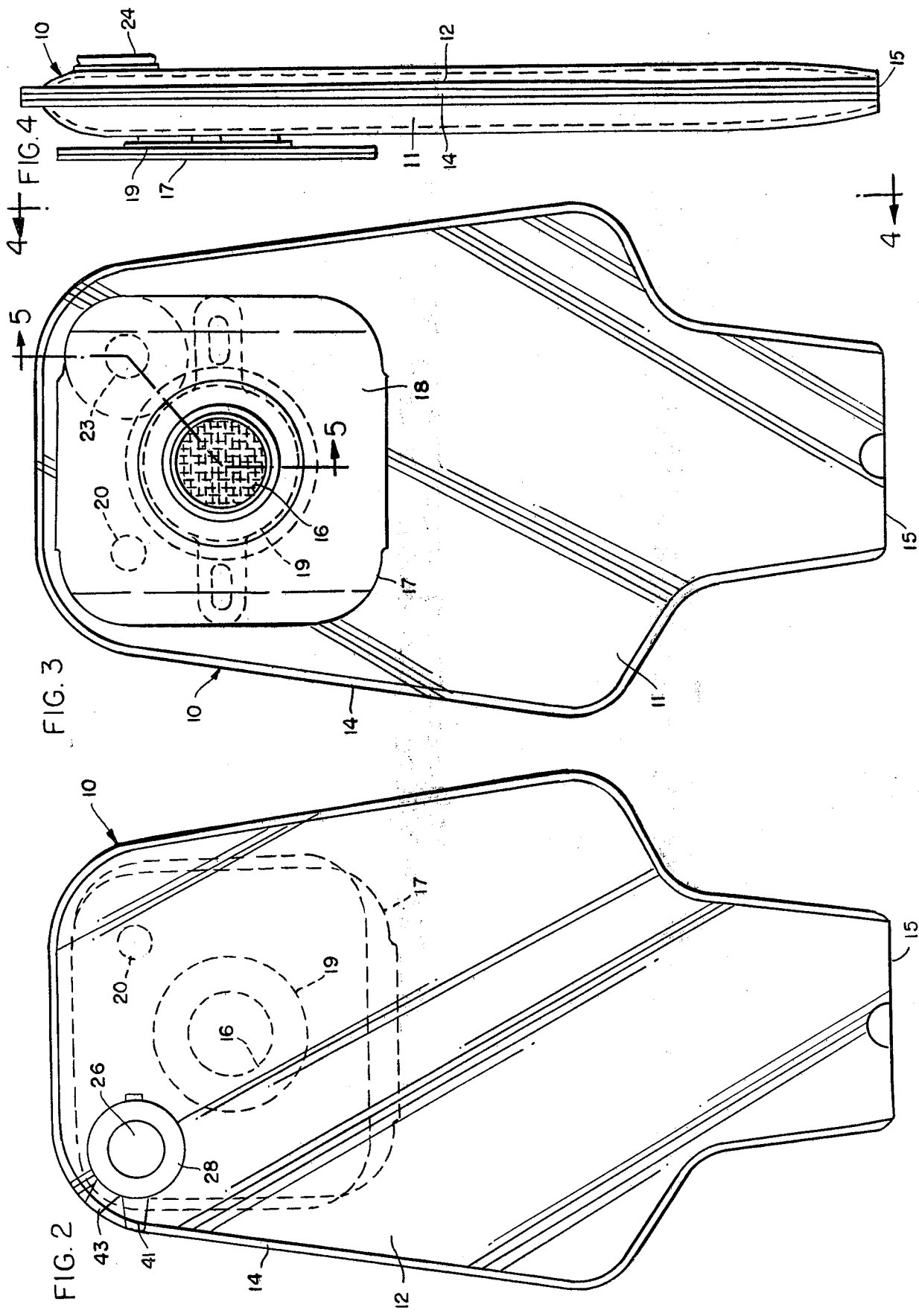

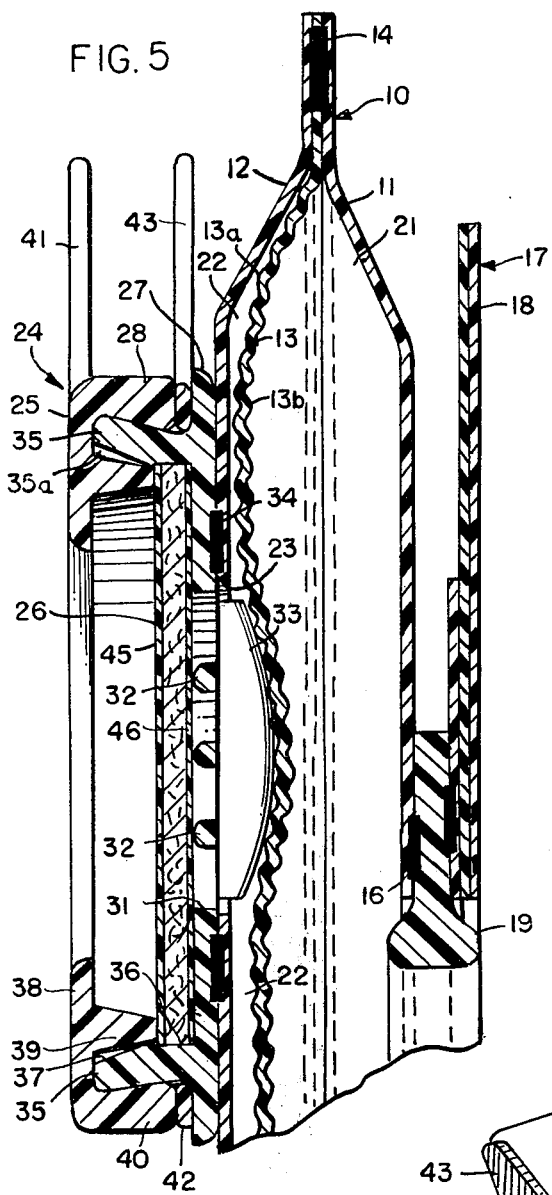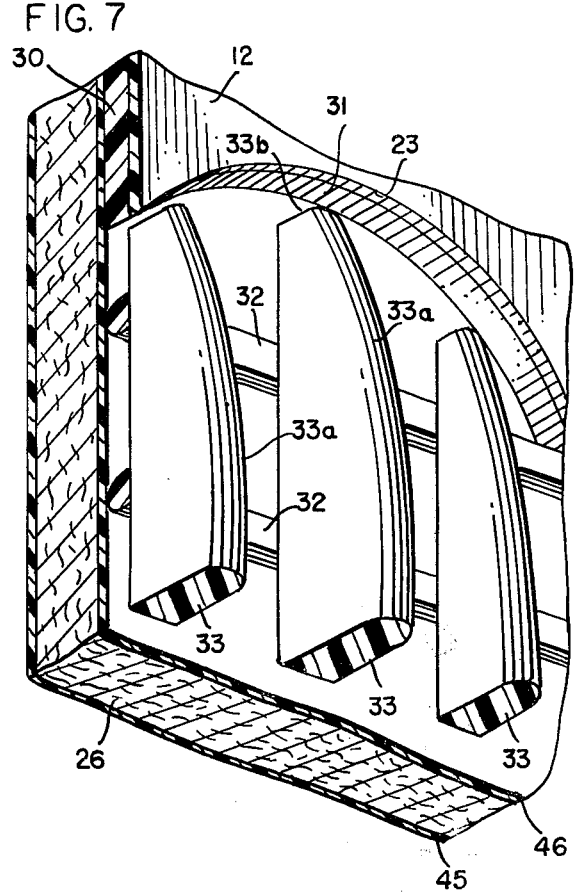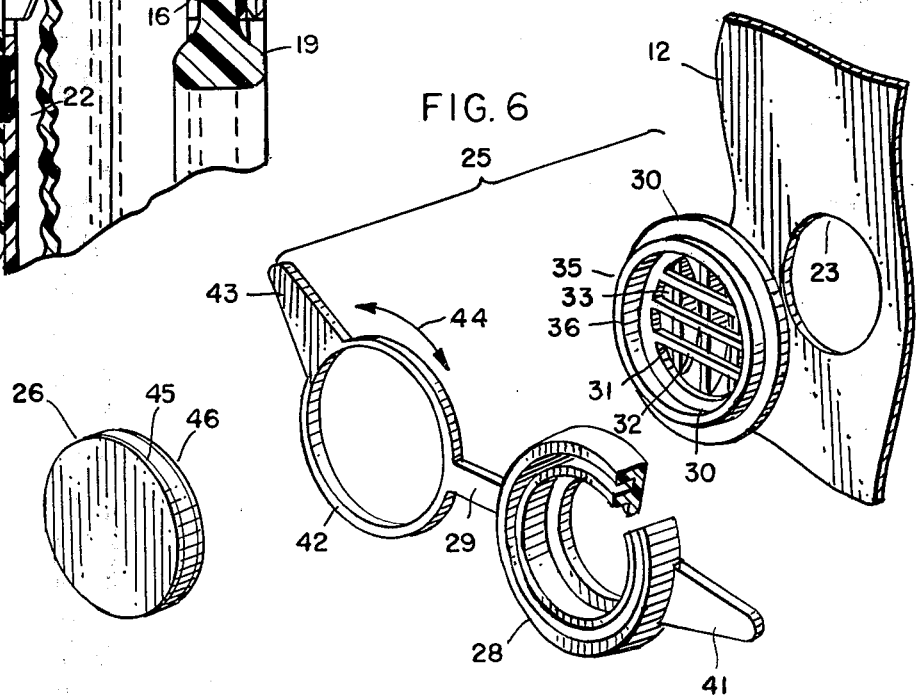

DRAINABLE COLLECTION POUCH AND FILTER ASSEMBLY THEREFOR

BACKGROUND AND PRIOR ART

Patents such as U.S. Pat. Nos. 4,280,498 and 3,039,464 relate to urostomy or ileostomy appliances that may be worn by patients for extended periods (commonly four to seven days) and must therefore be drained periodically. Such an appliance typically lacks the gas vent and filter sometimes found in non-drainable short-term pouches (as disclosed, for example, in U.S. Pat. Nos. 3,084,091, 3,439,677, 3,759,260, and 4,203,445) because of the danger that in a long-term drainable pouch such a filter might become clogged by liquids or solids, resulting in blockage of gas flow from the pouch and possible rupture of the wall thereof, or separation of the adhesive seal against the patient's skin, or leakage through or about the filter element. Therefore, the wearer of a conventional drainable pouch must periodically deflate the pouch, either by cracking open the discharge port, peeling away a portion of the adhesive patch sealing the pouch to the skin surface, or puncturing a hole in the pouch with a pin or other instrument. Such procedures are inconvenient and may lead to additional inconveniences and difficulties. If the pouch is deflated by opening the discharge port, the wearer must also be prepared to cope with the release of liquids from the pouch. Should the bag be deflated by peeling back a portion of the adhesive patch, secure reattachment of the detached portion may be difficult to achieve, and should the wall of the bag be punctured, the hole must then be sealed by tape or other suitable means. All of these procedures require an ostomate to interrupt normal activities and find seclusion to reach the pouch, relieve flatus buildup, and then reseal the pouch to avoid discomfort and embarrassment from escaping odors, fluids, and/or solids.

Other patents relating to vented pouches and illustrative of the art are U.S. Pat. Nos. 3,055,368, 2,054,535, 2,555,086, 3,952,727, and 4,274,848.

SUMMARY OF THE INVENTION

A main aspect of this invention lies in providing a drainable collection pouch having an automatic gas-venting and deodorizing filter assembly which is effectively protected against clogging in normal use. The result is a drainable collection appliance that does not require an ostomate to interrupt normal activities (including sleeping) for the purpose of periodically opening, puncturing, or partially detaching a pouch to relieve gas buildup therein.

Another aspect of this invention lies in providing a vented drainable collection pouch having a deodorizing filter which may be easily and quickly replaced when the filter has lost its deodorizing effectiveness. Despite the ease with which the filter may be removed and replaced, the filter element, when disposed within its holder, is effectively retained in a manner that virtually eliminates the possibilities of the filter being bypassed by outflowing gases.

In brief, the collection appliance comprises a pouch having a pair of thermoplastic front (outer) and rear (inner) side walls and an intermediate barrier wall disposed therebetween. All of the walls are heat sealed together along their superimposed peripheral edges to provide the pouch with a pair of adjacent chambers separated by the intermediate barrier wall. The rear wall has a stoma opening disposed along the vertical midline of the pouch, and adhesive attachment means extends about the opening for sealing the pouch to a patient. An aperture is provided in the intermediate barrier wall at a point spaced laterally from the stoma opening and at an elevation no lower than that opening when the pouch is supported vertically. A gas discharge port is located in the front wall at a point spaced laterally from the aperture in the barrier wall; hence, gas entering the bag through the stoma opening must flow laterally through one chamber to pass through the aperture of the intermediate barrier wall, and then laterally in the opposite direction through the next chamber to pass through the gas discharge port. An odor-adsorbing filter element is removably mounted in a holder located at the gas discharge port.

Selected surface areas of the walls are provided with embossed geometric patterns to prevent the openings of the respective walls from becoming blocked by adjacent walls and, in general, to prevent the walls from sticking together when the pouch is in use. Additionally, the filter holder at the gas discharge port of the front wall is provided with arcuate spacers to insure that the intermediate barrier wall cannot engage the filter element to block gas flow through that element. In the embodiment disclosed, such spacers take the form of ribs disposed in an intersecting geometric pattern, such ribs being constructed and arranged to promote effluent drainage into the lower portion of the pouch away from the filter assembly. The grid of intersecting ribs is also constructed to facilitate forward (or outward) flexure of the grid when ejection and replacement of a filter element are desired.

The replaceable filter element takes the form of a resilient, porous disc containing activated charcoal or other suitable odor adsorbent. The disc is secured within a holder having an annular body section perimetrically sealed to the front wall of the pouch and having a retaining ring section integrally connected to the body section. Both sections are formed of flexible thermoplastic material and may be snap-fitted together to secure the resilient filter element in place within the holder. A central aperture is provided in the body section, and the aforementioned spacer ribs are formed integrally with the body and bridge the aperture to retain the filter element and at the same time prevent direct contact between that element and the intermediate barrier film. Because of the hinged connection between the body and retaining ring sections, a user may easily open the holder to remove and replace the filter element without danger that the ring section might accidentally be detached, dropped, contaminated, damaged, and/or possibly lost. In a preferred embodiment, the body and ring sections are formed separately and are hingedly connected only after the body section is heat sealed to the front wall of the pouch. In addition to facilitating production, such a construction permits a user to rotate the ring section and position the tabs used for opening and closing the holder so that such tabs may be most conveniently positioned for either right or left handed operation.

Other feartures, advantages, and objects of the invention will become apparent from the specification and drawings.

DRAWINGS

FIG. 2 is an elevational view of the front side of the pouch.

FIG. 3 is an elevational view of the rear or patient-contacting side of the pouch.

FIG. 4 is an elevational view taken along line 4—4 of FIG. 3.

FIG. 5 is an enlarged sectional view taken along line 5—5 of FIG. 3.

FIG. 6 is an enlarged fragmentary exploded perspective view depicting the components of the filter assembly.

FIG. 7 is an enlarged fragmentary perspective view showing features of the spacer rib construction of the filter holder.

DETAILED DESCRIPTION OF PREFERRED EMBODIMENT

Figure 1:
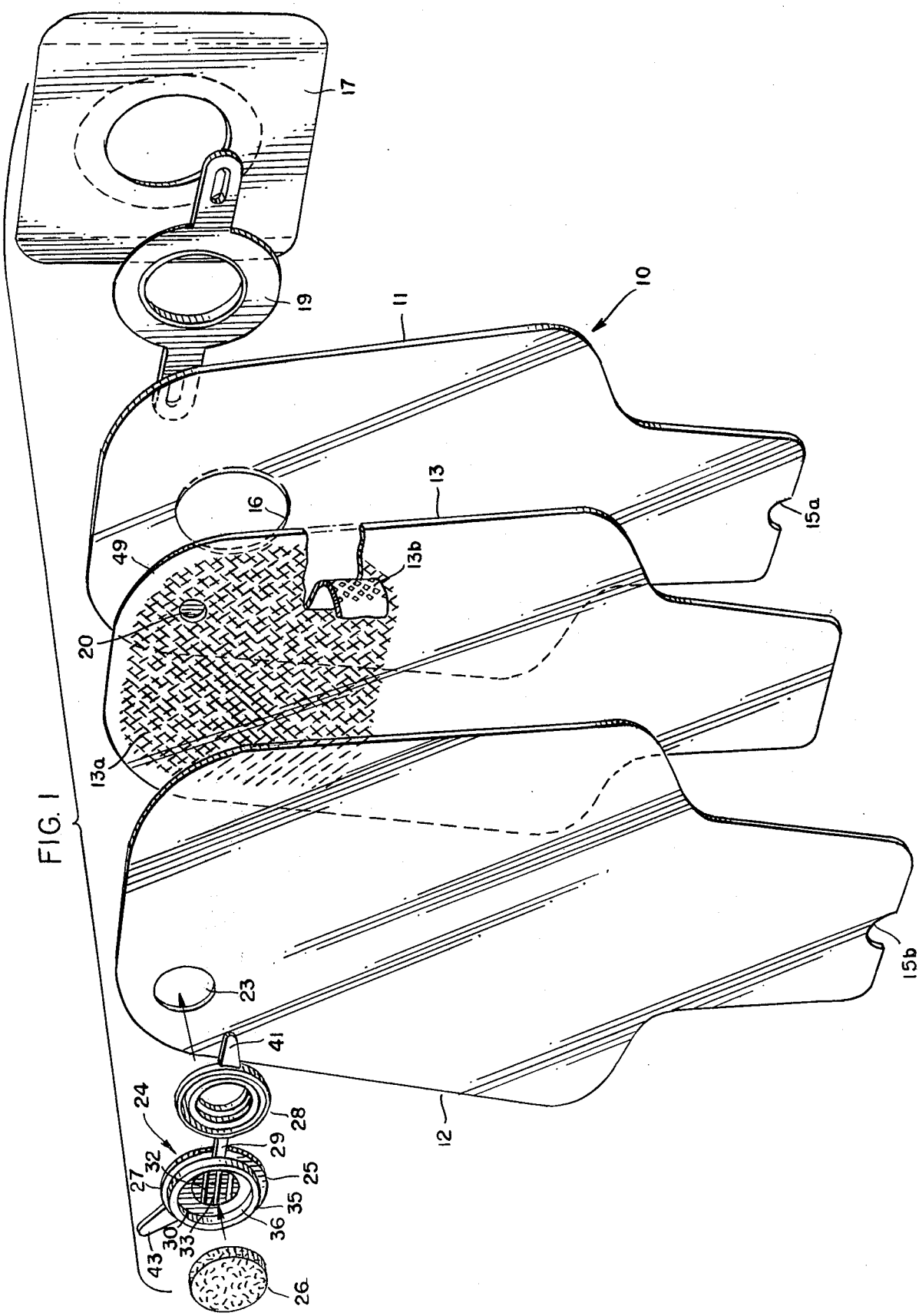
FIG. 1 is an exploded perspective view showing the components of a drainable collection pouch and filter assembly embodying this invention.

Referring to the drawings, the numeral 10 generally designates a drainable collection pouch having an inner or rear wall 11, an outer or front wall 12, and an intermediate barrier wall 13, all formed of thermoplastic film. The walls may be of similar dimensions, are juxtaposed in the relationship shown in FIG. 1, and have their side and top edges heat-sealed together as represented by numeral 14 in FIG. 5. The lower end of the pouch is tapered and terminates in a discharge opening 15. Walls 11 and 12 are provided with notches or recesses 15a and 15b, and wall 13 therebetween is left unnotched, to assist a user in spreading the walls for draining the pouch and, if necessary, for cleaning the inside surfaces at the pouch's lower end following a draining operation. In use, the pouch's lower end would be closed by a suitable clamping device such as the closure shown and described in Nolan U.S. Pat. No. 3,523,534. Alternatively, the pouch might be provided at its lower end with a valved drain assembly, such as the assembly disclosed in Jensen U.S. Pat. No. 4,280,498.

The film material for the ostomy pouch or bag 10 may be any effective gas and liquid impervious thermoplastic material such as, for example, a polyolefin film laminated with an appropriate barrier material. A particularly suitable commercial material comprises low density polyethylene coextruded with a coextensive layer or core of polyvinylidene chloride. Such material is commercially available under the designation "Saranex" from Dow Chemical Company, Midland, Mich.

The inner or rear wall 11 of the ostomy pouch, in accordance with standard practice, is provided with a stoma-receiving opening 16 surrounded by a patch 17 coated with a conventional pressure-sensitive medical adhesive (not shown). The adhesive coating upon the rear surface of the patch 17 is protected by removable backing sheets 18 which are stripped from the patch at the time of application. In the illustrated embodiment, a resilient gasket ring 19 is interposed between the attachment patch 17 and rear wall 11 of the pouch, the purpose of the resilient gasket being to form an effective seal about the stoma. Details of the stoma-receiving opening, the adhesive attachment patch, and the gasket, as well as attachment means which may take the form of a belt, are well known and are disclosed, for example, in co-owned U.S. Pat. Nos. 4,213,458, 3,822,704, 3,804,091, 3,759,260, and 3,523,534, the disclosures of which are incorporated by reference herein. Since such features do not constitute a direct part of this invention, further discussion herein is believed unnecessary.

Stoma-receiving opening 16 is located in the upper portion of the rear or inner wall 11 along the vertical midline of that wall. Referring to FIGS. 1-3, it will be observed that the intermediate barrier wall 13 has a relatively small aperture 20 located in the upper portion of that wall but displaced above and laterally with respect to stoma opening 16. Because opening 16 and aperture 20 are not aligned, and also because of the relatively small size of the aperture and its location above as well as to the side of opening 16, fluids (and semi-solid materials) discharged into the pouch through stoma opening 16 are not likely to pass through aperture 20. Instead, such materials will tend to drop into the lower portion of the rear chamber or compartment 21 (FIG. 5) between rear wall 11 and intermediate barrier wall 13. However, gases may readily flow laterally and upwardly within the rear chamber, passing through aperture 20 into front chamber 22.

The front or outer wall 12 is provided with a gas discharge port 23 at approximately the same elevation as aperture 22 in the barrier wall 13 but is located near the opposite side edge of the pouch. Gases passing through aperture 20 must therefore travel laterally through the front chamber to reach the outlet port 23. The serpentine path that gases entering stoma opening 16 must travel to pass through aperture 20 and then through port 23, and the size of chambers 21 and 22 into which such gases expand before exiting through port 23, prevent surges that might otherwise rupture or damage the filter assembly 24 mounted on the front wall at port 23 and, in general, promote effective gas filtering and venting operations. Moreover, should liquid or semi-solid matter happen to pass through aperture 20 into front chamber 22, the lateral spacing between the aperture located in the barrier wall near one side of the pouch and the discharge port 23 located in the front wall near the opposite side edge of the pouch greatly reduces the possibility that such material will reach port 23 and filter assembly 24. Such material would instead be expected to flow downwardly in chambers 22 and 21, collecting in the lower portions of those chambers, where it may be drained from the double chambers of the pouch when the clamping means (not shown) is removed from the pouch's opening lower end.

Filter assembly 24 is shown in FIG. 1 to consist essentially of a holder 25 and a filter element 26. The holder includes a body section 27 and a retaining ring section 28, the two sections being operatively connected by hinge strap 29. The body section 27 has a base wall 30 with a central opening 31 bridged by integral ribs 32 and 33 intersecting each other at substantially right angles in a grid pattern illustrated most clearly in FIGS. 6 and 7. It will be observed that the two sets of ribs do not extend in the same plane; specifically, that the ribs 32 are disposed in front of ribs 33. Ribs 33 are therefore spaced behind filter element 26 by the ribs 32 in contact with that element. In addition, ribs 33 have arcuate (and transversely rounded) rear surfaces 33a that project well behind the rear surface of base wall 30 and the rear surface of pouch wall 12 about port 23 (FIGS. 5, 7). The longitudinal and transverse curvatures of the rear surfaces of ribs 33 keeps the ribs from possibly damaging or adhering to the intermediate barrier wall 22 of the pouch. Ribs 32 and 33 therefore function as spacers for preventing the intermediate barrier film 13 from engaging filter element 26 and from sealing port 23. The spacer ribs also function to support the filter element 26 and prevent it from being displaced rearwardly through port 23. The ribs effectively prevent obstruction of the gas pathway through the discharge port and filter assembly and, at the same time, allow liquid and semi-solid material to drain downwardly within front chamber 22 away from the gas discharge port and filter element.

Such drainage is promoted because the two sets of ribs 32 and 33 extend along adjacent parallel planes rather than in the same plane, and because ribs of one of the sets have arcuate longitudinal rear surfaces 33a that for their full length are spaced well behind the inner surface of pouch wall 12 about port 23. Flowable effluent that might otherwise become trapped in the openings or windows of the grid is free to escape in generally horizontal or vertical directions when the ribs are oriented as shown in FIG. 7. It is to be noted, however, that the ribs need not be oriented as depicted for such draining to occur; it has been found that effective draining will take place if the grid is oriented so that ribs 33 extend vertically, or horizontally, or at some angle between horizontal and vertical, and that therefore it is unnecessary to select a particular rib orientation at the time the filter holder 25 is secured to the front wall 12 of the pouch.

The base wall 30 of the body section 27 of the holder is secured to the front wall 12 by an annular heat seal line or zone 34 (FIG. 5). Therefore, to escape from front chamber 22 through the port 23 in the pouch's front wall, gases must pass through the central opening 31 in the body section of the filter holder 25.

Referring to FIG. 7, it will be seen that the ends 33b of arcuate ribs 33 terminate short of the narrow surface of base wall 30 defining opening 31. Only the transverse ribs 32 completely bridge that opening. Such a construction not only promotes drainage of effluent from within opening 31, but also allows limited forward and rearward flexing of the grid within that opening. Such flexing is useful in manually ejecting a filter element from the holder, as described hereinafter.

The body section 27 of the holder also includes an annular flange 35 that projects forwardly and outwardly from base wall 30 and, together with that base wall, defines a chamber or recess 36 for receiving the disc-shaped filter element 26. As depicted in FIG. 5, the rearwardly and radially-outwardly projecting flange 35 is receivable in an annular channel 37 formed in retaining ring section 28. In its closed position, the ring section has a front wall portion 38 and a pair of concentric inner and outer side wall portions 39 and 40, respectively. The annular channel 37 defined by these wall portions extends forwardly and radially-outwardly when the retaining ring section is in its clamped or closed position (FIG. 5). Detachment of the ring section 28 from flange 35 requires deformation of the flange 35 and wall portion 40; hence, a snap-fit is provided between the ring and body sections, and separation of such sections is accomplished only by forces substantial enough to cause deformation of the plastic sections. While the resistance to such forces is easily enough to prevent unintentional separation of the sections, intentional separation may be readily achieved by gripping tab 41 and tab 43 and exerting an outwardly and forwardly directed force on outer wall portion 40 of the ring section, while bracing the body section against movement, to peel the ring section away from the locking flange of the body section.

In the embodiment illustrated, the filter holder 25 is formed in two parts that are joined together after base wall 30 has been heat sealed to the front wall of the pouch about discharge port 23. The construction is shown most clearly in FIG. 6. Hinge strap 29 is connected to a narrow snap ring 42 dimensioned to fit tightly about flange 35 immediately adjacent base wall 30 (FIG. 5). The ring must be stretched slightly, or the flange 35 must be deformed, or both, in order to snap the ring into its final position. Such attachment is facilitated by the radial tab 43 formed integrally with snap ring 42.

The two-part construction not only simplifies manufacture but also permits the snap ring 42 to be rotated with respect to flange 35 and base wall 30 (in the directions indicated by arrow 44 in FIG. 6) after the parts are fully assembled. Such rotation is achieved by urging tab 43 circumferentially in one direction or the other. The snap ring 42, and the retaining ring section 28 formed integrally with it, may therefore be rotated in a position that the user finds most convenient for performing the actions of opening and closing the filter holder. It will be observed from FIG. 2 that tabs 41 and 43 do not bear the same angular orientation when the filter holder is closed; consequently, a user may easily grip each of the tabs at the same time to shift the retaining ring 28 between its open and closed positions.

The filter holder 25 may be formed of any suitable polymeric material having the requirements of flexibility, toughness, and durability. Polyethylene has been found effective, but other thermoplastic materials such as polypropylene or polyvinyl chloride may be used.

The disc-shaped filter element is porous and may either be fibrous in construction or may be in the form of an open-celled plastic foam. In the preferred embodiment, the disc, in addition to venting and filtering, contains an adsorbent such as activated carbon to deodorize gases passing through the filter element. Reference may be had to co-owned U.S. Pat. No. 4,274,848 for details on the construction of a filter element formed of thermoplastic fibers (fibrillated polyethylene) coated with finely-divided activated carbon by means of a latex binder. Ideally, the filter element 26 has its opposite faces covered by layers 45 and 46 of a suitable gas-permeable but water-resistant barrier material of the type described in the aforementioned patent, the disclosure of which is incorporated herein by reference.

The deformable and resilient filter element 26 is dimensioned so that in an uncompressed or undeformed state its diameter is slightly greater than the smallest diameter of recess of chamber 36 of the filter holder. As shown in FIG. 5, the inner surface 35a of flange 35 at the mouth of chamber 36 tapers inwardly and rearwardly. The diameter of element 26 is less than the maximum diameter of that chamber but greater than the generally cylindrical portion of the chamber immediately adjacent base wall 30. Consequently, a user may easily insert a filter element into the enlarged mouth of the chamber. As the retaining ring section 28 is then shifted into its closed position, the inner wall portion 39 of that ring forceably engages the peripheral portion of the resilient filter element and urges the element into the reduced portion of the chamber. Radially inward compressive forces are exerted on the filter element to produce an effective seal between the periphery of that element and the reduced inner surface of flange 35.

When removal of a filter element is desired, the user simply disengages the retaining ring from the flange of the body section, swings the retaining ring into its open position, and then by finger (usually thumb) pressure applied in a forward direction against rear wall 11 of the pouch, flexes the grid of ribs 32–33 forwardly within opening 31 to displace the filter element 26 forwardly within chamber 35. The edge of the filter element 26 may then be easily gripped between the fingers and the element extracted from the chamber of the holder.

Referring to FIGS. 1 and 5, the intermediate barrier wall 13 is shown to have embossed areas 13a and 13b along its inner and outer surfaces. The embossed areas surround aperture 20 and extend well beyond the limits of stoma opening 16 and discharge port 23. The ridges and depressions of the geometric pattern insure that surface contact between the upper portion of the barrier film and the upper portions of rear and front walls 11 and 12, respectively, will not prevent gases from traveling through the pouch from stoma opening 16 to gas discharge port 23. It will be noted that the embossed surface areas terminate short of the outer limits of the intermediate wall 13 to leave a narrow planar border zone 49 for heat sealing to the front and rear walls of the pouch.

In the embodiment illustrated in the drawings, the areas of pattern embossing are located on the front and rear surfaces of intermediate barrier wall 13. If desired, similar areas of embossing may be provided on the inner surface of front wall 12, in which case the embossing of the intermediate barrier layer might even be eliminated. In any event, one of the opposing surfaces of the respective walls 12 and 13 in the upper portion of chamber 22 should be embossed to prevent such surfaces from sealing or sticking together and thereby blocking the flow of gases from aperture 20 to discharge port 23. Also, in the form shown in the drawings, intermediate barrier wall 13 is substantially coextensive in length (height) with rear and front walls 11 and 12; however, if desired, the lower portion of the barrier wall may terminate well above discharge opening 15. While such a construction may have the disadvantage of allowing some exudate to pass beneath the barrier wall from chamber 21 to chamber 22, that disadvantage may be avoided, if it is deemed necessary to do so, by heat sealing or otherwise sealing the lower edge of the barrier wall directly to the wall supporting filter assembly 24 (i.e., front wall 12 in the embodiment depicted) so that the only (or at least primary) communication between chambers 21 and 22 is through upper aperture 20.

While in the foregoing we have disclosed an embodiment of the invention in considerable detail for purposes of illustration, it will be understood by those skilled in the art that many of these details may be varied without departing from the spirit and scope of the invention.

We claim:

1. An ostomy pouch having front and rear walls, and an intermediate barrier wall therebetween, all formed of thermoplastic film; said walls having edges sealed together to provide said pouch with a pair of adjacent chambers separated by said intermediate barrier wall; said rear wall having a stoma opening disposed generally along the vertical midline of said rear wall; adhesive sealing means provided by said rear wall for peristomal sealing engagement with a wearer; a vent aperture in said intermediate wall at a point spaced laterally from said stoma opening and disposed at an elevation no lower than said stoma opening when said pouch is supported vertically; a gas discharge port in said front wall at a point spaced laterally from said aperture; a filter element; and means supporting said filter element at said discharge port; at least one of said walls being embossed in the area of said pouch in which said stoma opening, vent aperture, and discharge port are located to prevent said walls from blocking together and obstructing the flow of gases through said chambers.

2. The pouch of claim 1 in which said embossed wall is said intermediate barrier wall, the embossing thereof comprising patterns of surface undulations on opposite sides of said intermediate barrier wall.

3. The pouch of claim 1 in which said means supporting said filter element at said discharge port comprises a filter holder externally secured to said front wall about said port.

4. The pouch of claim 3 in which said filter holder includes spacer means projecting rearwardly through said gas discharge port for engaging said intermediate barrier wall and for preventing said barrier wall from engaging said filter element and from blocking the flow of gases through said port and filter element.

5. The pouch of claim 4 in which said spacer means comprises a plurality of ribs provided by said filter holder and projecting rearwardly through said port beyond said front wall.

6. The pouch of claim 4 in which said filter holder includes a body section sealed to said front wall about said gas discharge port and defining a forwardly-facing recess removably receiving said filter element; said body section having ribs defining a grid extending across said port for supporting said filter element; said spacer means comprising rearward extensions of at least some of said ribs.

7. The pouch of claim 6 in which said rearward extensions of said ribs are arcuate.

8. The pouch of claim 7 in which the ribs of said grid are arranged in groups extending at substantially right angles to each other; said ribs of only one of said groups having said arcuate rearward extensions.

9. The pouch of claim 8 in which the ribs of one of said groups have their opposite ends freely spaced from the perimeter of said port, said filter holder being formed of flexible plastic material, whereby, said grid may be flexed forwardly and rearwardly within said port upon the application of forces causing flexure of the other of said ribs.

10. The pouch of claims 8 or 9 in which said arcuate rearward extensions of the ribs of said one group define rear surfaces spaced behind the rear surface of the front wall of said pouch immediately about said port.

11. The pouch of claims 8 or 9 in which said ribs of the respective groups extend along adjacent parallel planes with the ribs of said one group providing rear surfaces spaced substantially behind the rear surfaces of the ribs of the other group, and said ribs of said other group having front surfaces spaced substantially in front of the front surfaces of said ribs of said one group.

12. The pouch of claim 6 in which said filter holder also includes a flexible retaining ring section engagable with said body section to retain a filter element within said recess.

13. The pouch of claim 12 in which said retaining ring section and said body section are hingedly connected to each other.

14. The pouch of claim 13 in which said body section is provided with a forwardly-projecting annular flange extending about said filter element and said ring section is provided with an annular channel tightly but releasably receiving said flange.

15. The pouch of claim 14 in which said filter element is resilient and circular in outline; said filter element in an undeformed state having a diameter slightly larger than the smallest diameter of said recess of said body section, whereby, said filter element is in a state of radial compression when secured within said filter holder.

16. The pouch of claim 15 in which said retaining ring section includes an integral tab projecting radially therefrom for shifting said hinged retaining ring section into and out of its closed position.

17. The pouch of claim 16 in which said body section includes an integral tab portion projecting radially therefrom for bracing said body section when said retaining ring section is shifted between closed and open positions; said tabs of said ring and body sections being out of angular alignment with respect to each other when said ring section is in its closed position.

18. The pouch of claim 14 in which said body section of said filter holder includes a snap ring extending about and retained by said flange; said snap ring being integrally formed with said retaining ring section and being connected thereto by an integral hinge strap extending therebetween.

19. An ostomy pouch having front and rear walls, and an intermediate barrier wall therebetween, all formed of thermoplastic film; said walls having edges sealed together to provide said pouch with a pair of adjacent chambers separated by said intermediate barrier wall; said rear wall having a stoma opening disposed generally along the vertical midline of said rear wall; adhesive sealing means provided by said rear wall for peristomal sealing engagement with a wearer; a vent aperture in said intermediate wall at a point spaced laterally from said stoma opening and disposed at an elevation no lower than said stoma opening when said pouch is supported vertically; a gas discharge port in said front wall at a point spaced laterally from said aperture; a filter element; and a filter holder externally sealed to said front wall about said gas discharge port and removably supporting said filter element at said port.

20. The pouch of claim 19 in which said filter holder includes spacer means projecting rearwardly through and beyond said gas discharge port for engaging said intermediate barrier wall and for preventing said barrier wall from engaging said filter element and from blocking the flow of gases through said port and filter element.

21. The pouch of claim 20 in which said spacer means comprises a plurality of ribs provided by said filter holder and projecting rearwardly through said port beyond said front wall of said pouch.

22. The pouch of claim 20 in which said filter holder includes a body section sealed to said front wall about said gas discharge port and defining a forwardly-facing recess removably receiving said filter element; said body section having ribs arranged in groups extending at substantially right angles to each other to define a grid extending across said port; said spacer means comprising rearward extensions of the ribs of one of said groups.

23. The pouch of claim 22 in which said rearward extensions provide rearwardly-facing smoothly-contoured arcuate surfaces.

24. The pouch of claim 23 in which the rear limits of said arcuate surfaces along the full length of each rib of said one group are spaced behind the inner surface of the front wall of said bag about said port.

25. The pouch of claim 24 in which said ribs of said one group are supported by the ribs of the other group and have end surfaces freely spaced from the periphery of said port; said body section being formed of flexible polymeric material, whereby, said grid is capable of being flexed forwardly and rearwardly with respect to said port upon the application of forces causing flexure of the ribs of said other group.

26. The pouch of claims 24 or 25 in which said ribs of said other group are disposed in front of said ribs of said one goup; said ribs of said other group having front surfaces engagable with said filter element for supporting said element and spacing the same from the front surfaces of the ribs of said one group.

27. The pouch of claim 22 in which said filter holder also includes a flexible retaining ring section engagable with said body section to retain said filter element within said recess.

28. The pouch of claim 27 in which said retaining ring section and said body section are hingedly connected to each other.

29. The pouch of claim 28 in which said body section is provided with a forwardly-projecting annular flange extending about said filter element and said retaining ring section is provided with an annular channel tightly but releasably receiving said flange.

* * * * *